(12) United States Patent
Jakoby

(10) Patent No.: US 6,765,392 B1
(45) Date of Patent: Jul. 20, 2004

(54) METHOD AND DEVICE FOR EVALUATING A SENSOR DEVICE

(75) Inventor: Bernhard Jakoby, Vienna (AT)

(73) Assignee: Robert Bosch GmbH, Stuttgart (DE)

( * ) Notice: Subject to any disclaimer, the term of this patent is extended or adjusted under 35 U.S.C. 154(b) by 0 days.

(21) Appl. No.: 10/149,544

(22) PCT Filed: Oct. 18, 2000

(86) PCT No.: PCT/DE00/03652
§ 371 (c)(1),
(2), (4) Date: Aug. 27, 2002

(87) PCT Pub. No.: WO01/42762
PCT Pub. Date: Jun. 14, 2001

(30) Foreign Application Priority Data

Dec. 7, 1999 (DE) ........................... 199 58 769

(51) Int. Cl.⁷ .............................................. G01R 27/32
(52) U.S. Cl. .................................... 324/633; 324/639
(58) Field of Search .................... 73/54.01, 32 A, 73/53.01, 579; 324/639, 633, 691

(56) References Cited

U.S. PATENT DOCUMENTS 5,686,841 A    11/1997  Stolarczyk et al.
6,397,661 B1 *  6/2002  Grimes et al. ............. 73/24.06
6,650,959 B1 * 11/2003  Bouvyn ....................... 700/143

FOREIGN PATENT DOCUMENTS

JP          08 050 115       2/1996

* cited by examiner

*Primary Examiner*—N. Le
*Assistant Examiner*—Waltewr Benson
(74) *Attorney, Agent, or Firm*—Kenyon & Kenyon

(57) ABSTRACT

A method and a device for analyzing a sensor device, in which the sensor device forms an electric resonator in an oscillating circuit energized with an external energization voltage. The current in the oscillating circuit is detected in the range of the resonant frequency, and then the current thus detected is multiplied by the external excitation voltage. Finally, the signal obtained by this multiplication is averaged.

17 Claims, 3 Drawing Sheets

METHOD AND DEVICE FOR EVALUATING A SENSOR DEVICE

FIELD OF THE INVENTION

The present invention relates to a method and a device for analyzing a sensor device, the sensor device forming an electric resonator in an oscillating circuit energized by an external excitation voltage.

Although applicable to any sensor devices, the present invention as well as the principles on which it is based are explained here with respect to a viscosity sensor device.

BACKGROUND INFORMATION

Piezoelectric thickness-mode shear transducers made of quartz, for example, have been used for measuring viscosity for some time now (see, for example, S. J. Martin et al., Sens. Act. A 44(1994) pages 209–218). When such a thickness-mode shear transducer is immersed in a viscous liquid, the resonant frequency of its natural oscillation and its attenuation vary as a function of the viscosity and density of the viscous liquid.

FIG. 4 shows an equivalent circuit diagram of a known viscosity sensor having a quartz resonator. R in FIG. 4 denotes the viscosity sensor or "resonator" in general. In the electric equivalent circuit diagram, TA denotes the dry component and FA the liquid component. Dry component TA has a series circuit composed of a capacitor $C_1$, an inductor $L_1$ and a resistor $R_1$. The liquid component has a series circuit of an inductor $L_2$ and a resistor $R_2$. Dry component TA and liquid component FA are bridged by an additional capacitor $C_0$.

In liquid component FA, resistance $R_2$ is proportional to $\sqrt{\eta\rho}$, where $\eta$ is the dynamic viscosity and $\rho$ is the density of the viscous liquid. $R_2$ represents the viscous attenuation by the liquid. $L_2$ produces the frequency shift due to the viscous liquid, which is also proportional to $\sqrt{\eta\rho}$. In the case of rough resonator surfaces, $L_2$ also contains components generated by "trapped" liquid components in the rough resonator surface. In the case of a known or sufficiently constant density $\rho$, the quartz resonator may therefore be used to determine viscosity $\eta$.

According to the publication by S. J. Martin et al. cited above, these variable electric parameters $R_2$ and $L_2$ may be detected by using resonator R as the frequency-determining element in an oscillator. As an alternative, the impedance spectrum may be determined in the vicinity of the resonant frequency (see Lec et al., Proc. IEEE Ultrasonics Symp. (1997) pages 419–422).

FIG. 5 shows such a known analyzer circuit for the known viscosity sensor according to FIG. 4.

A voltage controlled oscillator VCO is used, which supplies resonator R which is immersed in a liquid, namely oil in this case. The output signal of resonator R is mixed with a reference signal REF in a multiplier M.

Finally, the d.c. component of the resulting signal is determined via a low-pass filter TP. The curve of this output signal over the frequency of voltage controlled oscillator VCO is ultimately used to evaluate the oil viscosity.

This evaluation is performed in a computer 100, which also controls voltage controlled oscillator VCO.

One disadvantage of the known approaches described above is that in characterizing highly viscous liquids, resistance $R_2$ increases greatly, so that in the vicinity of the series resonant frequency the impedance of the resonator is determined to a great extent by capacitance $C_0$ and by leakage capacitance $C_S$ in parallel to it also. This makes it difficult to determine the relative equivalent parameters by using an oscillator or impedance spectroscopy. One possible expedient is connecting an inductor in parallel to compensate for $C_0$ and $C_S$ in the vicinity of the series resonant frequency of the resonator. One disadvantage here is the required balancing plus the fact that leakage capacitance $C_S$ varies under some circumstances.

The method according to the above publication by Lec et al. allows at least partial compensation for the effects of $C_0$ and $C_S$, depending on the nature of the reference branch, but it does not yield an output signal corresponding to viscosity, but instead it is used only to determine a characteristic frequency response which is determined by viscosity.

SUMMARY OF THE INVENTION

The method according to the present invention and the corresponding device have the advantage over the known approach that the corresponding circuits are also suitable for measurement of highly viscous liquids. The sensor output signal is an easily processable direct voltage as a measure of the viscosity of the liquid.

The present invention is based on the idea that the interfering influence of static resonator capacitance $C_0$ and leakage capacitances $C_S$ is eliminated by determining the amplitude of the resistive in-phase component of the resonator current at the series resonant frequency.

According to a preferred embodiment, the current is detected by a measuring shunt connected to ground.

According to another preferred embodiment, the amplitude of the resistive component of the resonator current is determined by multiplying a signal which corresponds to the resonator current by the external excitation voltage and then filtering the result to form an average value.

According to another preferred embodiment, the external excitation voltage is wobbled, and the peak value of the signal corresponding to the average value is retained with a time constant which is greater than the period of the wobble frequency.

According to another preferred embodiment, the external excitation voltage is frequency modulated (e.g., with a small square-wave signal). This produces amplitude fluctuations in the signal corresponding to the average value. The signal corresponding to the average value is used together with the modulation signal to regulate the excitation mid-frequency to the resonant frequency.

According to another preferred embodiment, the sensor device is a viscosity sensor and has a determination device for determining viscoelastic effects based on the output signal of the first low-pass filter and the output signal of the regulating device.

According to another preferred embodiment, at least one of the multiplication devices is implemented in the circuitry by a switched inverter.

According to another preferred embodiment, the detection device for detecting the current in the oscillating circuit is a transimpedance amplifier.

DETAILED DESCRIPTION

In the figures the same reference numbers denote the same components or those having an identical function.

Figure 1:
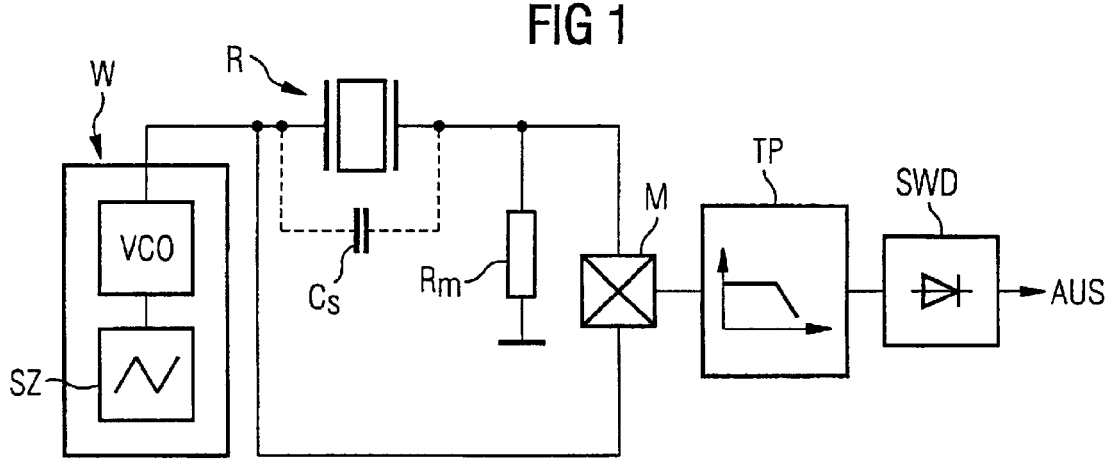
FIG. 1 shows a block diagram of a first embodiment of the analyzer device according to the present invention.

FIG. 1 shows a block diagram of a first embodiment of the analyzer device according to the present invention.

FIG. 1 shows a wobble device W for wobbling the external power supply voltage. VCO is a voltage controlled oscillator controlled by a saw-tooth voltage generator SZ. R denotes the resonator in general, $C_S$ is a leakage capacitance and $R_m$ is a measuring shunt connected to ground. M is a multiplier which mixes the output signal of detection resistor $R_m$ and the output signal of wobble device M together. TP is a low-pass filter which receives the output signal of multiplier M, and SWD is a peak value detector which receives the output signal of low-pass filter TP and ultimately supplies output signal AUS which corresponds to the viscosity.

In particular, the resonator current through measuring shunt $R_m$ is determined and multiplied by the applied resonator voltage. The average value of the resulting signal is proportional to the amplitude of the in-phase component of the resonator current and may be determined by filtering through a low-pass filter. This eliminates the influence of the reactive current component determined by $C_0$ and $C_S$.

Figure 4:
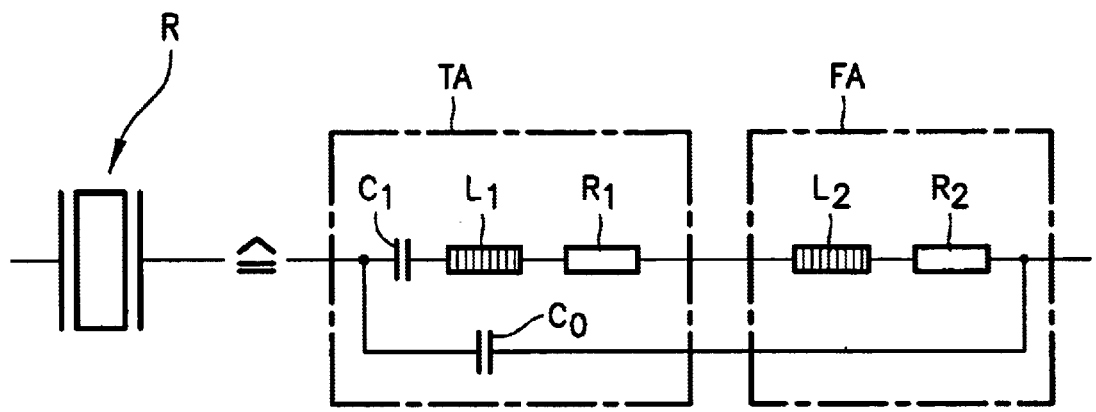
FIG. 4 shows an equivalent circuit diagram of a known viscosity sensor.
Figure 5:
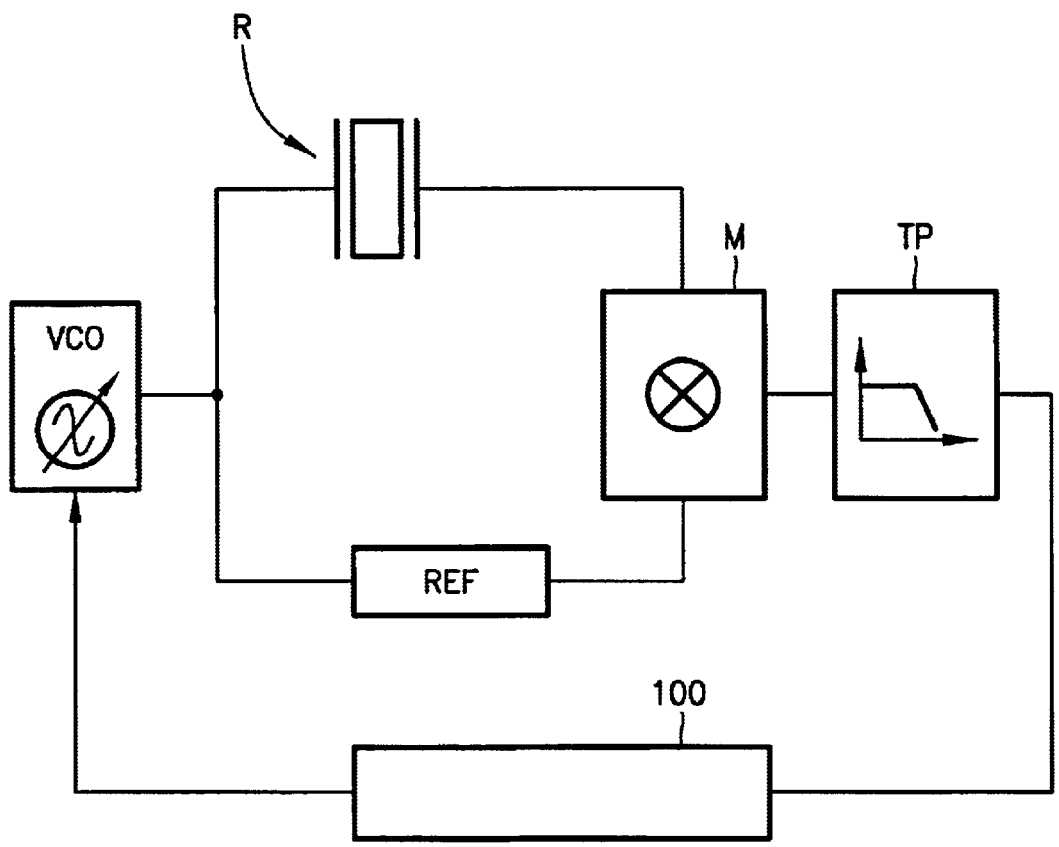
FIG. 5 shows a known analyzer circuit for the known viscosity sensor according to FIG. 4.

The exact function of the circuit having this design for determination of viscosity is as follows. Resonator R is supplied by wobble device W. In wobbling or tuning of frequency, a maximum of low-pass filter TP signal is obtained at the series resonant frequency of resonator R and may be used to determine resistance $R_2$ which is determined by the viscosity (see FIG. 4). This maximum at the output of low-pass filter TP is detected using peak value detector SWD and used as output signal AUS for determination of viscosity. The memory time constant of peak value detector SWD is greater than the period of the wobble frequency of wobble device W.

Figure 2:
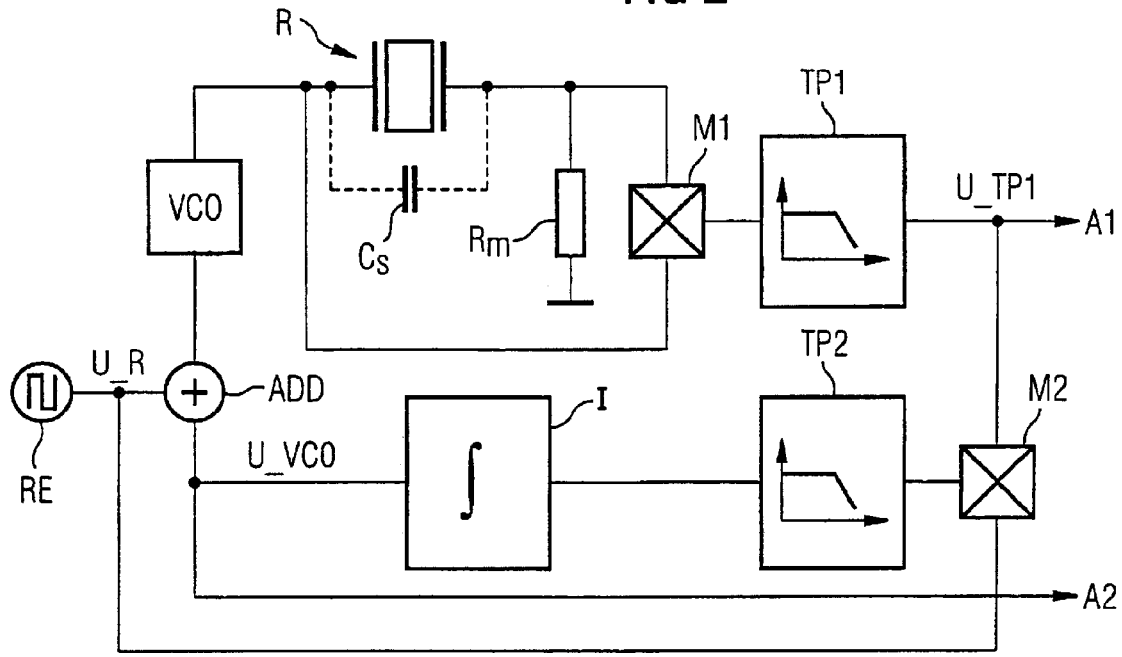
FIG. 2 shows a block diagram of a second embodiment of the analyzer device according to the present invention.

FIG. 2 shows a block diagram of a second embodiment of the analyzer device according to the present invention.

In addition to reference notation already introduced, M1 in FIG. 2 denotes a first multiplier, TP1 denotes a first low-pass filter, U_TP1 denotes the output signal of first low-pass filter TP1, M2 denotes a second multiplier, TP2 denotes a second low-pass filter, I is an integrator, U_VCO is the output signal of integrator I, ADD is an adder, RE is a square-wave signal generating device for generating a modulation voltage U_R, and A1 and A2 are a first and a second output signal, respectively.

In this second embodiment, voltage controlled oscillator VCO may also be tuned by a regulating circuit to the resonant frequency of resonator R as an alternative to the wobble method according to the first embodiment. At the series resonance, signal U_TP1 at the output of first low-pass filter TP1 is at a maximum and therefore may not be used directly as an input quantity of a linear regulator.

Figure 3:
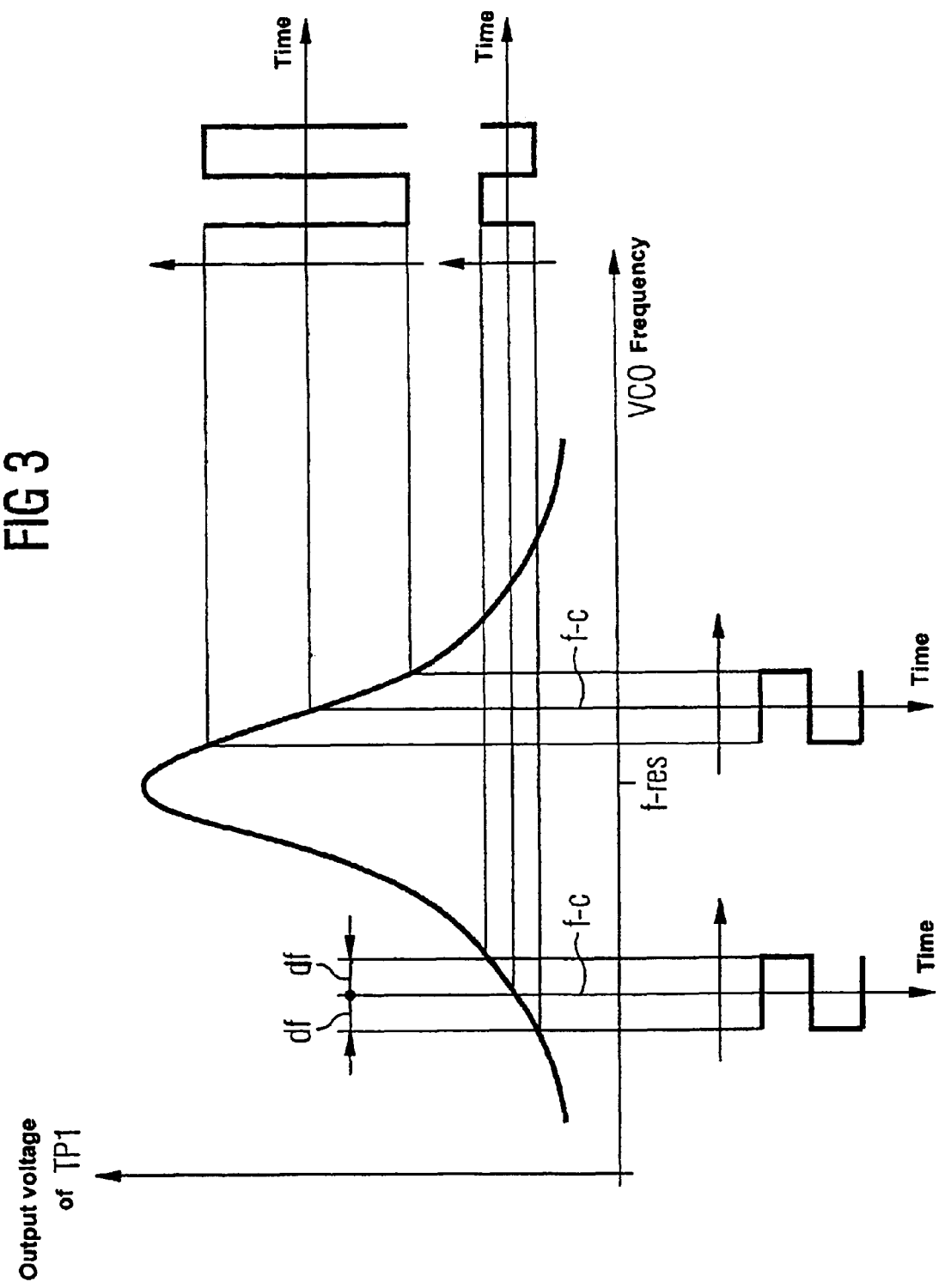
FIG. 3 shows a diagram of the output voltage of the first low-pass filter as a function of the VCO frequency in the second embodiment of the analyzer device according to the present invention as illustrated in FIG. 2.

Therefore, in this embodiment, the frequency of voltage controlled oscillator VCO is varied, i.e., frequency modulated periodically about a mid-frequency f_c. This is illustrated in FIG. 3, which is a diagram of the output voltage of the first low-pass filter as a function of the VCO frequency in the second embodiment of the analyzer device according to the present invention as illustrated in FIG. 2.

In the case in question, this is accomplished by superimposing a small square-wave signal of amplitude U_R on control voltage U_VCO of voltage controlled oscillator VCO. The instantaneous frequency of voltage controlled oscillator VCO then jumps periodically back and forth between values f_c+df and f_c−df, where f_c=k*U_VCO, and df=k*U_R, k being the constant of voltage controlled oscillator VCO.

Thus a direct voltage having a square-wave voltage superimposed on it is obtained at the output of first low-pass filter TP1, i.e., signal U_TP1. The latter is in-phase or 180° out of phase with the modulated square-wave voltage, depending on whether f_c is below or above series resonant frequency f_res, as illustrated at the upper right of FIG. 3.

For f_c=f_res, the superimposed square-wave voltage disappears. Strictly speaking, this is true only in the case of a symmetrical frequency response about the resonant frequency, but if U_R has been selected to be small enough, this is true in first approximation for any frequency response.

Multiplication of output signal U_TP1 of first low-pass filter TP1 by modulation signal U_R and determination of the direct component by second low-pass filter TP2, whose cutoff frequency is much lower than the frequency of the square-wave signal (modulation signal) thus yield a positive voltage if frequency f_c>f_res and a negative voltage if frequency f_c<f_res.

Thus by using integrator I in the regulator, it is possible to obtain a regulating voltage U_VCO which sets f_c=f_res for voltage controlled oscillator VCO. In the regulated state, either output signal A1, i.e., U_TP1, or output signal A2, i.e., U_VCO, may be used as analog output signals corresponding to viscosity.

Output signals A1 and A2 correspond to the attenuation and the resonant frequency of the resonator, respectively. These two variables represent the viscosity of the liquid measured. Simultaneous observation of these variables also allows detection of viscoelastic (i.e., not purely viscous) liquid behavior, because in this case the ratio of the two variables varies in comparison with the purely viscous case.

According to another embodiment, the multiplier may be implemented in the form of a switched inverter in the circuitry. The analysis of the phase ratio is done for the functionality of the circuit. With all multipliers M, M1, M2 used here, one of the two input variables has a constant amplitude (excitation voltage in the case of M and M1, square-wave voltage in the case of M2).

To be more precise, the first input variable, namely the excitation voltage in the case of M and M1 or the square-wave voltage in the case of M2, is used to control a switch. The second input variable is inverted (first input variable negative), or not (first input variable positive), depending on the position of the switch.

Although the present invention has been described above on the basis of preferred embodiments, it is not limited to these embodiments but instead may be modified in a variety of ways.

In particular, the present invention is not limited to viscosity sensors but instead may be used with all sensors which are used as the element for determining the resonant frequency in an oscillating circuit energized with an external excitation voltage.

What is claimed is:

1. A method of reading a sensor device forming an electric resonator in an oscillating circuit which is energized in accordance with an external excitation voltage, comprising:

detecting a resonator current in a range around a resonance frequency;

multiplying the current by the external excitation voltage; and forming an average value of a signal originating from the multiplying;

wherein the external excitation voltage is wobbled, and a peak value of the signal corresponding to the average value is retained with a time constant that is greater than a period duration of a wobble frequency.

2. The method according to claim 1, wherein the current is detected by a measuring shunt connected to ground.

3. The method according to claim 1, further comprising:

ascertaining an amplitude of a resistive component of the current by multiplying a signal corresponding to the resonator current by the external excitation voltage, and subsequently filtering to form the average value.

4. A method of reading a sensor device forming an electric resonator which is energized in accordance with an external excitation voltage, comprising:

detecting a resonator current in a range around a resonance frequency;

multiplying the current by the external excitation voltage;

forming an average value of a signal originating from the multiplying;

frequency modulating the external excitation voltage so that corresponding amplitude fluctuations occur in the signal corresponding to the average value; and regulating an excitation mid-frequency to the resonant frequency in accordance with the signal corresponding to the average value together with a modulation signal.

5. The method according to claim 4, wherein the current is detected by a measuring shunt connected to ground.

6. The method according to claim 4, further comprising:

ascertaining an amplitude of a resistive component of the current by multiplying a signal corresponding to the resonator current by the external excitation voltage, and subsequently filtering to form the average value.

7. A device for reading a sensor device forming an electric resonator which is energized in accordance with an external excitation voltage, comprising:

a detection device for detecting a resonator current in a range around a resonance frequency;

a first multiplication device for multiplying the current detected by the external excitation voltage;

an averaging device for forming an average value of an output signal of the first multiplication device;

a wobble device for wobbling the frequency of the external excitation voltage; and a peak value detection device for detecting a peak value of an output signal of the first low-pass filter having a time constant that is greater than a period duration of a wobble frequency.

8. The device according to claim 7, wherein the detection device includes a measuring shunt connected to ground.

9. The device according to claim 7, wherein the averaging device includes a first low-pass filter.

10. The device according to claim 7, wherein the detection device includes a transimpedance amplifier.

11. A device for reading a sensor device forming an electric resonator which is energized in accordance with an external excitation voltage, comprising:

a detection device for detecting a resonator current in a range around a resonance frequency;

a first multiplication device for multiplying the current detected by the external excitation voltage;

an averaging device for forming an average value of an output signal of the first multiplication device;

a frequency modulation device for performing a frequency modulation of the external excitation voltage and resulting amplitude fluctuations in an output signal of the first low-pass filter; and a regulating device for regulating the oscillating circuit to the resonant frequency on the basis of the output signal of the first low-pass filter and a modulation signal.

12. The device according to claim 11, wherein the regulating device includes:

a second multiplication device for multiplying the output signal of the first low-pass filter by the modulation signal, a second low-pass filter for ascertaining a direct voltage component of an output signal of the second multiplication device, and an integration device for integrating an output signal of the second low-pass filter.

13. The device according to claim 12, wherein at least one of the first multiplication device and the second multiplication device includes a switched inverter.

14. The device according to claim 11, wherein the sensor device is a viscosity sensor and includes an ascertainment device for determining viscoelastic effects based on at least one of the output signal of the first low-pass filter and an output signal of the regulating device.

15. The device according to claim 11, wherein the detection device includes a measuring shunt connected to ground.

16. The device according to claim 11, wherein the averaging device includes a first low-pass filter.

17. The device according to claim 11, wherein the detection device includes a transimpedance amplifier.

* * * * *